United States Patent
Segal et al.

(10) Patent No.: US 11,207,267 B2
(45) Date of Patent: Dec. 28, 2021

(54) BIO-ADHESIVE DISSOLVING COMPOUNDS AND DEVICE

(71) Applicant: Segal Innovations LLC, Delray Beach, FL (US)

(72) Inventors: Bruce Segal, Delray Beach, FL (US); Nelson Landrau, Marlborough, MA (US)

(73) Assignee: Segal Innovations LLC, Delray Beach, FL (US)

( * ) Notice: Subject to any disclaimer, the term of this patent is extended or adjusted under 35 U.S.C. 154(b) by 156 days.

(21) Appl. No.: 16/591,005

(22) Filed: Oct. 2, 2019

(65) Prior Publication Data

US 2021/0100740 A1 Apr. 8, 2021

(51) Int. Cl.
| | |
|---|---|
| *A61K 9/00* | (2006.01) |
| *A61K 31/407* | (2006.01) |
| *A61L 31/10* | (2006.01) |
| *A61L 31/16* | (2006.01) |
| *A61K 47/32* | (2006.01) |

(52) U.S. Cl.
CPC .......... *A61K 9/0051* (2013.01); *A61K 31/407* (2013.01); *A61K 47/32* (2013.01); *A61L 31/10* (2013.01); *A61L 31/16* (2013.01)

(58) Field of Classification Search
None
See application file for complete search history.

(56) References Cited

U.S. PATENT DOCUMENTS

| | | | |
|---|---|---|---|
| 5,707,643 | A | 1/1998 | Ogura et al. |
| 9,474,645 | B2 | 10/2016 | Cui et al. |
| 2004/0170685 | A1 | 9/2004 | Carpenter et al. |
| 2005/0048121 | A1 | 3/2005 | East et al. |
| 2005/0129731 | A1 | 6/2005 | Horres et al. |
| 2008/0045911 | A1 | 2/2008 | Borgia et al. |
| 2009/0318549 | A1 | 12/2009 | Butuner |

(Continued)

FOREIGN PATENT DOCUMENTS

| | | | | |
|---|---|---|---|---|
| CA | 2572592 C | 2/2006 | | |
| EP | 1913962 A1 * | 4/2008 | ............. | A61L 31/16 |

(Continued)

OTHER PUBLICATIONS

Farag et al., "Effects of an autostable bicanaliculus intubation stent in the management of acquired punctal stenosis" Journal of Egyptian Opthalmological Society; 107, 2014, pp. 160-165; 6-pages.

(Continued)

*Primary Examiner* — Aradhana Sasan
(74) *Attorney, Agent, or Firm* — Christopher & Weisberg, P.A.

(57) ABSTRACT

A medical device may comprise a body including a mixture of polyvinylpyrrolidone ("PVP") and mitomycin. The medical device may be in any size or shape such that the medical device may be inserted into living tissue, including, but not limited to, a lacrimal punctal plug and a stent. The mixture of PVP and mitomycin may be coated on a portion of the medical device, contained within a cavity on the medical device, disposed on the surface of the medical device or configured as part of the medical device such that the mixture of PVP and mitomycin can be delivered to tissue.

14 Claims, 6 Drawing Sheets

(56) References Cited

U.S. PATENT DOCUMENTS

| | | | |
|---|---|---|---|
| 2010/0274224 | A1 | 10/2010 | Jain et al. |
| 2013/0102999 | A1* | 4/2013 | Looper ............ A61M 25/0068 604/528 |
| 2017/0020729 | A1 | 1/2017 | Jarrett et al. |
| 2019/0083307 | A1 | 3/2019 | Burns et al. |

FOREIGN PATENT DOCUMENTS

| | | | | |
|---|---|---|---|---|
| EP | 2614844 | B1 | 4/2015 | |
| EP | 2010096 | B1 | 7/2017 | |
| EP | 2276471 | B1 | 8/2018 | |
| KR | 20030004582 | * | 1/2003 | ............ A61L 29/16 |
| WO | 2011076924 | A1 | 6/2011 | |
| WO | 2016083891 | A1 | 6/2016 | |

OTHER PUBLICATIONS

Konuk et al., "Long-term Success Rate of Perforated Punctal Plugs in the Management of Acquired Punctal Stenosis" Ophthalmic Plastic and Reconstructive Surgery; vol. 24, No. 5, 2008, pp. 399-402, 4-pages.

Lam et al., "Mitomycin as Adjunct Therapy in Correcting Iatrogenic Punctal Stenosis" Ophthalmic Surgery; vol. 24, No. 2, 1993, pp. 123-124; consisting of 2-pages.

Ma'luf et al., "Mitomycin C as Adjunct Therapy in Correcting Punctal Stenosis" Ophthalmic Plastic and Reconstructive Surgery; vol. 18, No. 4. 2002, pp. 285-288, 4-pages.

Malet et al., "Clinical and scintigraphic comparison of silicone and polyvinylpyrrolidone coated silicone perforated plugs" Br J Ophthalmol; vol. 82, No. 12, 1998, pp. 1416-1419, consisting of 4-pages.

Bukhari, "Management Options of Acquired Punctal Stenosis" Saudi Med J; vol. 34, No. 8, 2013, pp. 785-792, consisting of 8-pages.

Soiberman et al., "Punctal Stenosis: Definition, Diagnosis, and Treatment" Clinical Ophthalmology, vol. 6, No. 1, 2012, pp. 1011-1018, consisting of 16-pages.

Krimsky et al., "Topical Mitomycin C is an Effective, Adjunct Therapy for the Treatment of Severe, Recurrent Tracheal Stenosis in Adults" J Bronchol, vol. 13, No. 3, 2006, pp. 141-143; consisting of 3-pages.

Jehangir et al., "Comprehensive Review of the Literature in Existing Punctal Plugs for the Management of Dry Eye Disease," Journal of Ophthalmology, vol. 2016, consisting of 23-pages.

Grundke et al., "Surface Functionalization of Silicone Rubber for Permanent Adhesion Improvement," Langmuir, 2008, vol. 24, No. 21, p. 12603-12611; consisting of 10-pages.

Danshiitsoodol et al., "The mitomycin C (MMC)-binding Protein from MMC-producing Microorganisms Protects from the Lethal Effect of Bleomycin: Crystallographic Analysis to Elucidate the Binding Mode of the Antibiotic to the Protein," J. Mol. Biol. 2006, vol. 360, No. 2, pp. 398-408; consisting of 11-pages.

Roy et al., "Bioadhesive Polymeric Platforms for Transmucosal Drug Delivery Systems—a Review," Tropical Journal of Pharmaceutical Research, 2010, vol. 9, No. 1, pp. 91-104, consisting of 14-pages.

Rabensteiner et al., "Collared Silicone Punctal Plugs Compared to Intracanalicular Plugs for the Treatment of Dry Eye," Current Eye Research, 2013, vol. 38, No. 5, pp. 521-525; consisting of 5-pages.

Mi et al., "High molecular Weight Povidone Polymer-Based Films for Fast-Dissolving Drug Delivery Applications," Drug Delivery Technology, 2007, vol. 7, No. 6, pp. 36-43; consisting of 8-pages.

Mao et al.,"Molecular Characterization and Analysis of the Biosynthetic Gene Cluster for the Antitumor Antibiotic Mitomycin C from Streptomyces lavendulae NRRL 2564," Chemistry and Biology, 199, vol. 6, No. 4, pp. 251-263; consisting of 13-pages.

Tost et al.,"Plugs for Occlusion of the Lacrimal Drainage System," Geerling G, Brewitt H (eds): Surgery for the Dry Eye. Developments in Ophthalmology, 2008, vol. 41, pp. 193-212; consisting of 20-pages.

Wang et al.,"Sulfonated-Polydimethylsiloxane (PDMS) Microdevices With Enhanced Electroosmotic Pumping and Stability," Can. J. Chem., 2006, vol. 84, pp. 720-729; consisting of 10-pages.

Hernan et al.,"Topical Mitomycin-C for Recalcitrant Esophageal Strictures: Anovel Endoscopic/Flouroscopic Technique for Safe Endoluminal Delivery," Journal of Pediatric Surgery, 2008, vol. 43, No. 5, pp. 815-818; consisting of 4 pages.

Wolf, Rory A., "Plastic Surface Modification Surface Treatment and Adhesion," Munich, Carl Hanser Verlag, 2010. Print.

Chen et al., "Film-Forming Polymers in Fast-Dissolving Oral Films," Poster presented at the 2006 Annual Meeting and Exposition of the American Association of Pharmaceutical Scientists, San Antonio, TX, October 29-Nov. 2, 2006; consisting of 5-pages.

* cited by examiner

Stability Study Result

| Film Stored in Ambient Temperatures or Refrigerated Temperatures | Weight (mg) of Film | Peak Area (Measured with High Pressure Liquid Chromotography "HPLC") | mg/ml | % MMC Original Film |
|---|---|---|---|---|
| Ambient: 1 Day Film (1/22/19) | 103.3 | 2237.090 | 0.046 | 0.44 |
| Refrigerated: 1 Day Film (1/22/19) | 106.4 | 2209.680 | 0.045 | 0.42 |
| Ambient: 11 Day Film (2/2/19) | 108.0 | 2679.530 | 0.055 | 0.50 |
| Refrigerated: 11 Day Film (2/2/19) | 102.9 | 2118.590 | 0.043 | 0.42 |
| Ambient: 21 Day Film (2/12/19) | 108.0 | 2728.910 | 0.056 | 0.51 |
| Refrigerated: 21 Day Film (2/12/19) | 102.9 | 2356.750 | 0.048 | 0.47 |
| Ambient: 101 Day Film (4/27/19) | 108.2 | 2365.240 | 0.045 | 0.41 |
| Ambient: 185 Day Film (7/22/19) | 96.0 | 2107.760 | 0.040 | 0.41 |

*FIG. 2*

BIO-ADHESIVE DISSOLVING COMPOUNDS AND DEVICE

CROSS-REFERENCE TO RELATED APPLICATION n/a

STATEMENT REGARDING FEDERALLY SPONSORED RESEARCH OR DEVELOPMENT n/a

FIELD OF INVENTION

The present application is related to a method and device with drug delivery capabilities.

BACKGROUND OF THE INVENTION

Mitomycins are a family of aziridine-containing natural products isolated from Streptomyces caespitosus or Streptomyces lavendulae. Mitomycin may be used to treat a variety of different types if disorders and conditions associated with the growth and spread of cells. The term "mitomycin" may include mitomycin A, mitomycin B, and mitomycin C.

Mitomycin can inhibit the growth of cells within the body. Various treatments have used mitomycin including in chemotherapy, for modulating wound healing after ophthalmological surgeries, and in the management of various corneal disorders. Patients have successfully treated and managed conditions and symptoms when using mitomycin including for pancreatic, stomach, breast, bladder, esophagus, lung, anal, and liver cancers, gastrointestinal strictures, endoscopic dacryocystorhinostomy, scarring issues, as well as to modify wound healing from glaucoma surgery and in corneal excimer laser surgery.

Patients and medical providers face a variety of different challenges when treatments incorporate mitomycin. For example, the costs associated with drug therapies that include mitomycin can be extremely expensive. Purchasing even a small quantity of mitomycin can cost a significant amount of money and can be difficult for a patient and/or medical provider to purchase. Also, the costs associated with medications are constantly increasing, which can lead some patients to be faced with the choice of purchasing basic necessities, paying for medications, and/or medical treatments which can significantly impact their activities of daily living. Many insurance companies will not cover the full cost of medical procedures and/or the drugs used during medical procedures and therefore patient's sometimes must to make difficult decisions.

Mitomycin is soluble in water and can undergo rapid degradation in certain solutions. With this rapid degradation, it can be difficult to deliver the drug effectively and efficiently to a patient, because of dose variations due to active pharmaceutical ingredient ("API") degradation. To avoid under dosing, treatments using mitomycin must be prepared shortly before use and then used in the treatment quickly to avoid the breakdown of the mitomycin. For example, if mitomycin is used as part of a chemotherapeutic regime, the mitomycin must be combined with the other drugs very shortly before use and/or administration. If the mitomycin is not used quickly, it can breakdown and can reduce the effectiveness of the treatment.

Also, mitomycin can be toxic to the medical provider and avoiding any contact with the drug is the safest option for a medical provider. Mitomycin may be harmful if it comes into contact with the skin, eyes, or is swallowed and is a suspected carcinogenic agent. Strict safety precautions are to be followed by medical providers when handling this drug. For example, protective gear is often worn by a medical provider when s/he comes into contact with mitomycin including protective gloves, protective clothing, eye protection, and face protection. Additionally, medical providers are advised to wash hands and other body parts thoroughly after handling or otherwise coming into contact with mitomycin, even if protective gear is worn.

When mitomycin is used during surgery, it is often applied to tissue using a sponge which does not provide targeted and direct treatment to particular tissue using the mitomycin. When applied using a sponge, the mitomycin can ooze out onto tissue and unnecessarily expose tissue to mitomycin that was not intended to come into contact with the drug. Medical providers often copiously irrigate the tissue that was unnecessarily exposed to the mitomycin to try and prevent harm to the tissue that was not intended to come into contact with the mitomycin.

SUMMARY

The present invention advantageously provides a method and system for a medical device for the delivery of drugs to a patient. A medical device may comprise a body including a mixture of polyvinylpyrrolidone ("PVP") and mitomycin.

In one aspect of the embodiment, the medical device may have the mixture of PVP and mitomycin coated on at least a portion of the body.

In one aspect of the embodiment, the medical device may further comprise an exterior coating where the mixture of PVP and mitomycin are coated with the exterior coating.

In one aspect of the embodiment, the exterior coating may be lubricious.

In one aspect of the embodiment, the body may include an elongate portion.

In one aspect of the embodiment, the elongate portion may have a first portion and a second portion. The first portion of the elongate portion may have a rounded first end.

In one aspect of the embodiment, the second portion has a second end, the second end being expandable from a first diameter to a second diameter.

In one aspect of the embodiment, the body may define a cavity, the mixture of the PVP and the mitomycin may be disposed within the cavity.

In one aspect of the embodiment, the medical device may further include a bioabsorbable membrane enclosing at least a portion of the cavity.

In one aspect of the embodiment, the body may have a surface, the surface including at least one aperture.

In one aspect of the embodiment, the medical device may be a lacrimal punctal plug.

In one aspect of the embodiment, the body may be a stent.

In another embodiment, the medical device may comprise an elongate body sized to be received within a lacrimal punctum; a cavity within at least a portion of the body, the cavity having at least one opening and at least a portion of the cavity including a mixture of PVP and mitomycin; and a bioabsorbable membrane enclosing the at least one opening.

In one aspect of the embodiment, at least a portion of the bioabsorbable membrane may be lubricious.

In one aspect of the embodiment, the elongate body may have a first portion and a second portion opposite the first portion. The elongate body may be cylindrical and taper in diameter from the first portion to the second portion.

In one aspect of the embodiment, the first portion may have a first end, the first end being expandable from a first diameter to a second diameter.

In one aspect of the embodiment, the elongate body may have a diameter and the first end has a first diameter that may be at least one of the group consisting of greater than, equal to, and less than the diameter of the elongate body. The second portion may have a second end opposite the first end with a second end diameter that is greater than the diameter of the elongate body.

In one aspect of the embodiment, at least one of the group consisting of the first end and the second end is collapsible.

In one aspect of the embodiment, the medical device may further include a bioabsorbable coating. The mixture of the PVP and mitomycin may be provided with the bioabsorbable coating.

In another embodiment, a method for inserting a medical device into living tissue where the method includes: inserting a body into a living tissue, the body including a mixture of polyvinylpyrrolidone ("PVP") and mitomycin; advancing the body in the living tissue; allowing the mixture of PVP and mitomycin to disperse in the living tissue; and removing the body from the living tissue.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 illustrates a stability studies results for PVP films containing mitomycin;

DETAILED DESCRIPTION

Figure 1:
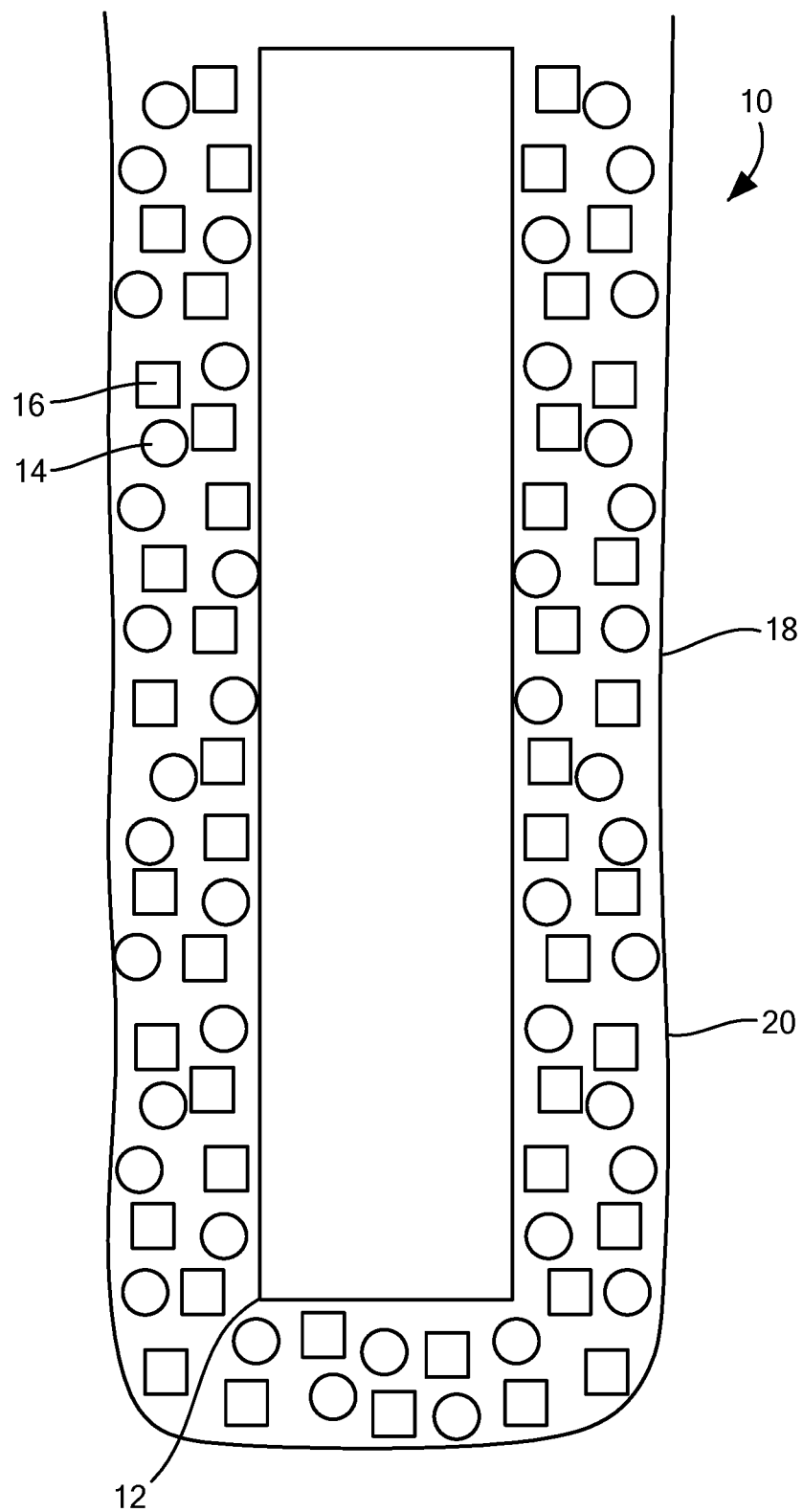
FIG. 1 illustrates an embodiment of a medical device in accordance with the present invention.

The system and methods disclosed herein are for a device and system for the delivery of compounds using water-soluble bio-adhesive dissolving polymers. Specifically, described herein are medical devices that can have various bio-adhesive dissolving compounds. While the figures show exemplary medical devices that can be used with the bio-adhesive dissolving compounds, these are non-limiting examples of water soluble bio-adhesive dissolving compounds that can be used with a variety of other and different medical devices.

Before describing in detail exemplary embodiments that are in accordance with the disclosure, it is noted that components have been represented, where appropriate, by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an", and "the" are intended to include the plural forms as well, unless the context clearly indicates otherwise. It will be further understood that the terms "comprises," "comprising," "includes", and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

It should be understood that various aspects disclosed herein may be combined in different combinations than the combinations specifically presented in the description and accompanying drawings. It should also be understood that, depending on the example, certain processes or methods described herein may be performed in a different sequence, may be added, merged, or left out altogether.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Referring now to the drawings in which like reference designators refer to like elements, there is shown in FIG. 1, an exemplary medical system constructed in accordance with the principles of the present application and designated generally as "10." The medical device 10 may have a body 12 and the body 12 may be any size and may have any myriad of shapes depending on how and where the body 12 and medical device 10 is to be used in a patient. For example, as shown in FIG. 1, the body 12 may be an elongate body configured to be inserted into an orifice or other body tissue. The body 12 may include a mixture of polyvinylpyrrolidone ("PVP") 14 and mitomycin 16. The mixture of PVP 14 and mitomycin 16 may be coated on at least a portion of the body 12. Alternatively, the mixture of PVP 14 and mitomycin 16 may be coated on the entire body 12. How and where the mixture of PVP 14 and mitomycin 16 is coated may depend upon what the mitomycin 16 is being used to treat and where in the body the mitomycin 16 is being used. For example, if the mixture of PVP 14 and mitomycin 16 is being used in an eye, this may require a different coating of the mixture than if it is being used in a medical device 10 that is to be inserted into the bladder.

Continuing to refer to FIG. 1, when PVP 14 is mixed with mitomycin 16 this mixture can create a bio-adhesive film 18 that can hold the mitomycin 16 in place, stabilize the mitomycin 16, and release the mitomycin 16 when water, or aqueous body fluids are added to the mixture of PVP 14 and mitomycin 16. For example, if the mixture of PVP 14 and mitomycin 16 are added to a patient's tissue that includes water or aqueous body fluids, the mitomycin 16 may be released from the mixture. An exterior coating 20 may also coat the mixture of PVP 14 and mitomycin 16 on the medical device 10. This exterior coating 20 may be lubricous or alternatively it may not be slippery.

Continuing to refer to FIG. 1, when referring to mitomycin 16 in the application, this may refer to mitomycin A, mitomycin B, and/or mitomycin C. Mitomycin 16 is soluble in water at 0.5 mg/mL at a pH of between 6.0 and 7.5. Also, mitomycin 16 may undergo rapid degradation in acidic solutions with a pH of less than 6 and when exposed to light. In general, mitomycin 16 is unstable and may only last up to one week when refrigerated between 2° C. and 8° C. without being exposed to light. When mitomycin 16 is formulated with PVP, the mixture of mitomycin 16 and PVP 14 may be stable for long periods of time. Mitomycin 16 alone is a very unstable compound and decomposes very quickly. This can make it difficult to use the mitomycin 16 in medical treatments as it breaks down quickly. However, when mitomycin 16 is mixed and/or blended with PVP 14 this mixture may be made into a film. As seen in FIG. 2, the active pharmaceutical ingredient ("API") API/polymer matrix is stable under ambient temperatures as well as with the presence of humidity for weeks at a time. Bio-adhesive structures composed of PVP 14 and mitomycin 16 stabilizes the mitomycin 16 for long-periods of time and slows down the decomposition of the mitomycin 16. As a non-limiting example, the API/polymer matrix is stable in a plastic or aluminum envelope, protected from light under ambient temperature as well as in the present of ambient humidity (<30% relative humidity) for weeks at a time. This slowing down of the decomposition of the mitomycin 16 may be for weeks, months, and/or years.

Now referring to FIG. 2, this table is an exemplary stability study showing the stability of the mixture of mitomycin 16 and PVP 14. The study was done over a one-hundred and eighty-five (185) day period and demonstrates the stability of this mixture over this period of time. In this exemplary stability study, a mitomycin 16 solution may be prepared using 30 mg of mitomycin and 29.970 grams of absolute ethanol. 1.0 mg/gram of the mixture of the 30 mg of mitomycin and 29.970 grams of absolute ethanol may be added to 1.360 grams of Kollidon-90F (PVP) and 0.090 grams of Kollidon®-VA64 (PVP copolymer). This mixture which includes PVP 14 and mitomycin 16 may be used to cast and/or coat films of the mixture on a medical device 10 to create a drug delivery structure. After the films dry, they may be divided into two or more sets, one set may be stored under "ambient temperatures" and the second set may be stored at a temperature ("refrigerated") of between 2° C. -8° C. In this exemplary study, an initial analysis of each film's API was made the same day that the films were created and each film contained 0.84 mg of mitomycin 16 per grams of polymer (PVP 14). Analysis of the mitomycin 16 was done for both ambient and refrigerated samples at eleven (11) days after the start, twenty-one (21) days after the start, and one-hundred and one (101) days after the start, and for the ambient temperature samples one-hundred and eighty-five (185) days after the creation of the films.

Continuing to refer to FIG. 2, the analysis of the films at ambient temperatures and at the refrigerated temperature of between 2° C.-8° C. showed that the films were stable and there were no significant changes to the API concentration. As seen in FIG. 2, the sample at the "ambient" temperature one (1) day after the creation of the film had 0.046 mg/ml and the "refrigerated" temperature sample had 0.045 mg/ml. One-hundred and one (101) days after the films were made, the "ambient" temperature films showed approximately a 2-5% decomposition of the mitomycin 16. The percentage change in the mitomycin 16 content was within the limits of experimental error, indicating that very little to no change in the mitomycin 16 content of the films occurred. One-hundred and eighty-five (185) days after the films were created showed that the films stored at the ambient temperature had not changed since the films were last looked at 101 days after the films were created. Ultimately, the mixture of the PVP 14 and the mitomycin 16 was shown to be stable for at least 185 days in ambient temperatures.

For example, The PVP 14 and mitomycin 16 mixture may be used with solutions including methanolic and ethanolic solutions. Although PVP 14 may be added to the mitomycin 16 as a mixture, other compounds may be added to the PVP 14 and mitomycin 16 mixture or may be added to the mitomycin 16 alone including, but not limited to, alginate, karaya gum, hydroxyethyl cellulose, hydroxypropyl cellulose, cellulose either, gelatin, polyvinyl alcohol, a biodegradable matrix, and/or another water based polymer. All of these materials may be used in combination with the mitomycin 16 to create a bio-adhesive film.

Figure 3A:
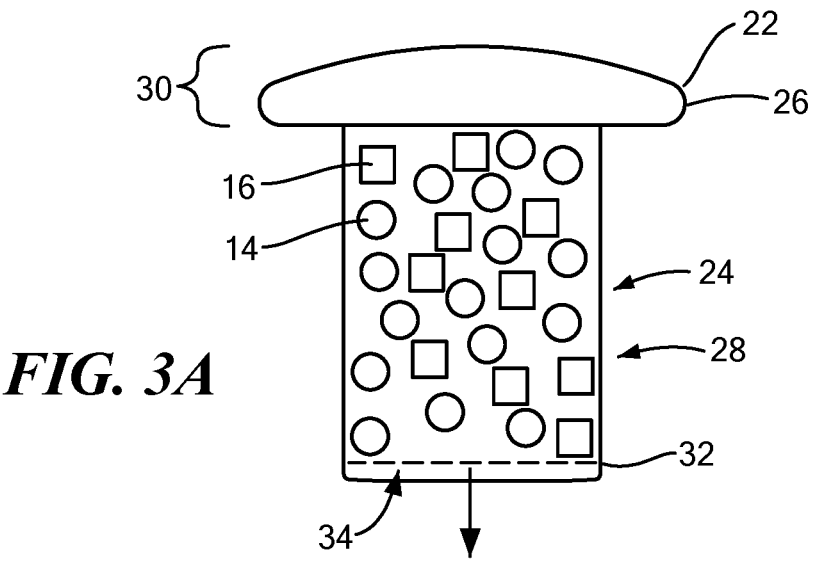
FIGS. 3A and 3B illustrate another embodiment of the medical device in accordance with the present invention.
Figure 3B:
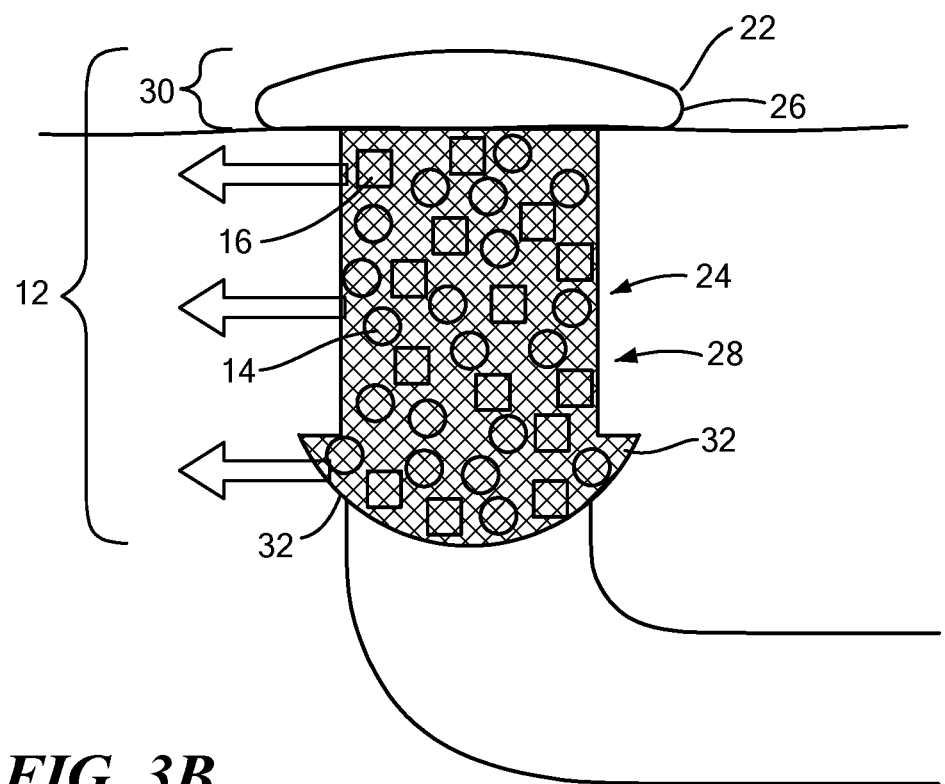

As shown in FIGS. 3A and 3B, the medical device 10 may be a lacrimal punctual plug 22. The lacrimal punctal plug 22 may be made out of material including polytetrafluoroethylene ("PTFE"), silicone rubber (polydimethyl siloxane), hydroxyethylmethacrylate ("HEMA"), and/or polymethylmethacrylate ("PMMA"). Also, the lacrimal punctal plug 22 may be coated with PVP 14 alone to make the surface of the punctal plug 22 slick, to prevent debris from collecting on the surface, and to enhance drainage. Some lacrimal punctal plugs 22 available on the market are coated with PVP 14 alone. Generally, lacrimal punctal plug 22 diameters may range from 0.3 millimeters ("mm") to 1.3 mm and have a length of between 1.0 mm and 2.0 mm, depending upon the size and dimensions required by the particular patient. The diameter and the length of the punctal plug 22 may be larger or smaller than the dimensions provided depending upon the particular patient. One or more than one punctal plug 22 may be used in the eye, such as in the corner of the eye.

Continuing to refer to FIGS. 3A and 3B, at least a portion of the punctal plug 22 may be coated with the mixture of PVP 14 and mitomycin 16. The punctal plug 22 may be treated with surface treatment methods, which may be used to improve adhesion of the PVP 14 and mitomycin 16 coating to the punctal plug 22 surface, may include using corona plasma discharge where a voltage between 10 to 20 kV may be applied through an air gap to ionize the atmospheric air which can create a polar group thereby increasing surface tension and functionalizing the surface, a chemical plasma discharge where plasma is generated using a low, a high, or a microwave frequency electric field by controlling the chemistry and pressure of the surrounding atmosphere, or with a flame plasma treatment where natural gas is burned and creates a flame that oxidizes the surface which results in the formation of hydroxyl, carboxyl, and carbonyl functionalities. These surface treatment coating methods, as well as others, may be used with different weights and line speeds and the coating adhesion strength to the punctal plug 22 may depend on how long after the particular treatment the coating of PVP 14 and mitomycin 16 mixture is applied. Alternatively, these surface treatment coating methods may not be used and the PVP 14 and mitomycin 16 mixture may be coated directly onto an untreated surface.

Continuing to refer to FIGS. 3A and 3B, in an exemplary embodiment, the lacrimal punctal plug 22 may include the body 12 where the body 12 includes an elongate portion of the body 24. This elongate portion of the body 24 may be any size or shape depending upon where and how the medical device is being used in the care and treatment of a patient and the elongate portion of the body 24 may be sized to be received within a patient's lacrimal punctum. The elongate portion 24 may include a first portion 26 and a second portion 28. The first portion of the elongate portion of the body 24 may have a first end 30 and this first end may be rounded or blunted such that when the punctal plug 22 is inserted into the tear duct opening of an eye, the rounded first end 30 may fit securely inside the punctum to prevent the loss of the punctal plug 22 in the eye. The first end 30 may have a diameter that is greater than, equal to, and/or less than the diameter of the body 12. Alternatively, the first end 30 may be a variety of other shapes including having a point like a cone, a square based pyramid, or a tetrahedron shape such that it may pierce through tissue. Also, as a non-limiting example, the first end 30 may not have any of PVP 14 and/or mitomycin 16 so that the first end 30 may come in direct contact with eye ball and/or the tears of the eye and may minimize the amount of PVP 14 and/or mitomycin 16 that comes into contact with the tears and the eye.

Continuing to refer to FIGS. 3A and 3B, the second portion 28 of the elongate portion of the body 24 may have a second end 32 and the second end 32 may be expandable from a first diameter 34 as shown in FIG. 3A to a second diameter 36 as shown in FIG. 3B. The first diameter 34 may be larger or smaller than the second diameter 36. The first diameter 34 and the second diameter 36 may be greater than, less than, and/or equal to the diameter of the body 12 of the medical device 10. For example, as shown in FIG. 3A, the first diameter 34 may be smaller than the second diameter 36 such that when the medical device 10 is inserted into the tissue there is less obstruction and the medical device 10 is more streamlined to aid in insertion of the device. Once the medical device 10, such as the punctal plug 22, is inserted into the patient's tissue, as shown in FIG. 3B, the first diameter 34 may be expanded from the first diameter 34 to the second diameter 36 to help secure the medical device 10 in place or to put at least a portion of the medical device 10 into contact with particular tissue. In alternative embodiments, the first diameter 34 may be larger than the second diameter 36 such that when the medical device 10 is inserted into tissue it may create a larger orifice which can make it easier for the remainder of the medical device 10 to be inserted into the tissue. The sizing of the diameter may be dependent upon where and how the medical device 10 is to be inserted into tissue. Additionally, the first end 30 and/or the second end 32 may be collapsible and/or expandable and retractable to assist in the insertion and retention of the medical device 10 within the patient's tissue.

Continuing to refer to FIGS. 3A and 3B, the mixture of PVP 14 and mitomycin 16 may be coated onto at least a portion of the punctal plug 22. For example, at least a portion of the punctal plug 22 may be dipped into the mixture of PVP 14 and mitomycin 16, and then the mixture may be left to dry to form a flexible, clear, and almost colorless film on the punctual punctal plug 22. The punctal plug 22 may be dipped into the mixture of PVP 14 and mitomycin 16 one time or more than one time. For example, the elongate portion of the body 24 of the punctual plug 22 may be dipped into the mixture of PVP 14 and mitomycin 16 one time and then the mixture may be given time to dry. Once the mixture has dried on the elongate portion of the body 24 of the punctal plug 22, the elongate portion of the body 24 of the punctal plug 22 may be dipped a second time into the mixture of PVP 14 and mitomycin 16 and then this coated mixture may be left to dry on the punctal plug 22. The number of times the punctal plug 22 is dipped into the mixture will depend upon how much mixture is to be coated onto the medical device 10 as well as the thickness of this coating. This amount may depend upon where and how the punctal plug 22 is going to be delivered to living tissue.

Continuing to refer to FIGS. 3A and 3B, alternatively, the PVP 14 and mitomycin 16 mixture may be painted onto the surface of the punctual plug 22 using, for example, a brush. As a non-limiting example, the mixture of the PVP 14 and mitomycin 16 may be painted onto the elongate portion of the body 24 such that the mixture of the PVP 14 and mitomycin 16 are not on the first end 30. Additionally, the PVP 14 and mitomycin 16 mixture may be sprayed to coat the entire medical device 10 or a portion of the medical device 10. If a medical provider were to insert the lacrimal punctal plug 22 into a portion of the eye by coming into contact with the first end 30, the medical provider would not come into contact with the mixture of the PVP 14 and the mitomycin 16, thereby minimizing the exposure to mitomycin 16. The use of the mixture of mitomycin 16 and PVP 14 in the eye can reduce scar tissue by modifying wound healing by using a medical device 10 that has a very targeted application to specific areas of tissue.

Continuing to refer to FIGS. 3A and 3B, the mixture of PVP 14 and mitomycin 16 may be applied in the form of a film or a patch. As a non-limiting example, the film may be produced by taking the mixture of PVP 14 and mitomycin 16 and spreading it out onto a non-stick surface. For example, the non-stick film surface may include a coating with a fluoropolymer or any other non-stick surface. The film may dry on the non-stick surface and then be peeled off of the non-stick surface into the film or patch. The film or patch may be made into any size or shape, including by using scissors to cut and shape the film/patch. The film or patch may be placed on a surgical site of the body for the suppression of scarring reactions. When the film or patch is placed over the surgical site and exposed to water, for example within tissue, the film/patch may dissolve and deliver mitomycin 16 to the adjacent tissue.

Figure 4:
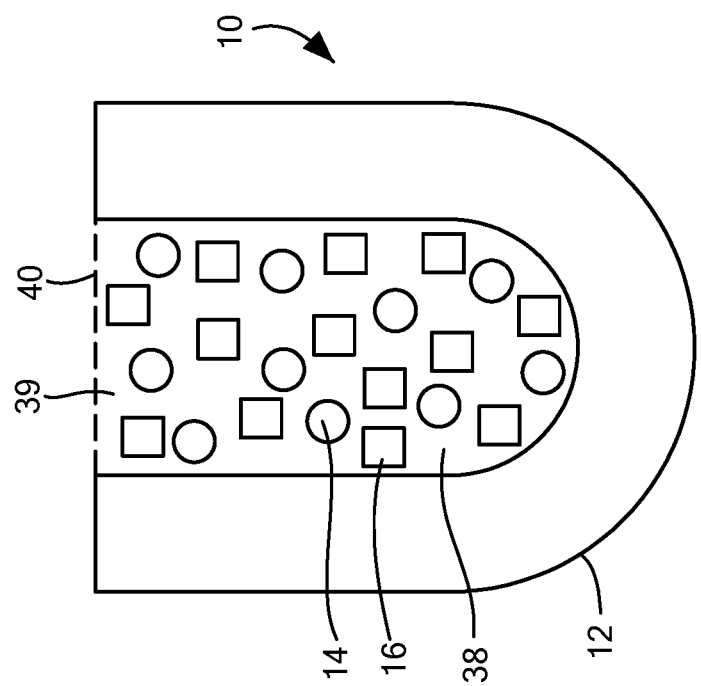
FIG. 4 illustrates another embodiment of the medical device in accordance with the present invention.

Now referring to FIG. 4, the body 12 may define a cavity 38 and the mixture of the PVP 14 and mitomycin 16 may be disposed within the cavity 38. The cavity 38 may have at least one opening 39. The amount and quantity of the mixture of the PVP 14 and mitomycin 16 contained within the cavity 38 may depend upon the size of the cavity 38. The cavity 38 may be filled with the mixture of PVP 14 and mitomycin 16 or only a portion of the cavity 38 may have the mixture of PVP 14 and mitomycin 16. The mixture of the PVP 14 and mitomycin 16 may also be disposed on any portion of the body 12 of the medical device 10. The medical device 10 may further include a bioabsorbable membrane 40 that may be configured to enclose at least a portion of the opening 39 of the cavity 38. Alternatively, the bioabsorbable membrane 40 may enclose the entire opening 39 of the cavity 38 or may be found in any portion of the cavity 38. The bioabsorbable membrane 40 may also coated on any portion of the medical device 10. For example, the bioabsorbable membrane 40 may be used to line a portion of the cavity 38 or all of the cavity 38. When the bioabsorbable membrane 40 is in place and enclosing the opening 39 of the cavity 38, it may secure the mixture of PVP 14 and mitomycin 16 within the cavity 38 before the medical device 10 is placed into living tissue. The bioabsorbable membrane 40 may be lubricious and may be configured to fully or partially enclose the opening 39 before the medical device 10 is inserted into body tissue. Once the medical device 10 is inserted into body tissue, the bioabsorbable membrane 40 may dissolve so that the mixture of PVP 14 and mitomycin 16 may be released into the tissue surrounding the medical device 10. The bioabsorbable membrane 40 may also provide protection to a medical provider that is involved in the handling of the medical device 10 with the mixture of PVP 14 and mitomycin 16 as well as with the insertion of the medical device 10 into living tissue.

Figure 5:
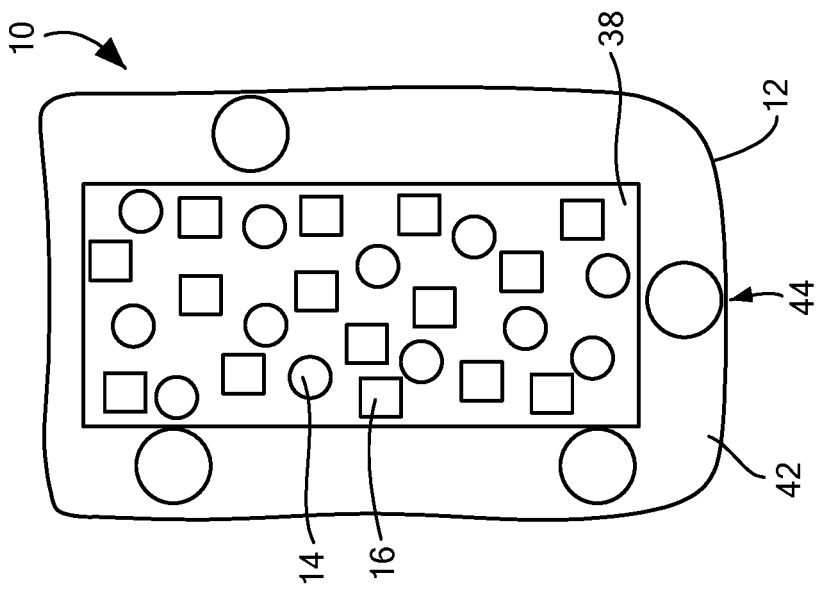
FIG. 5 illustrates another embodiment of the medical device in accordance with the present invention.

Now referring to FIG. 5, the medical device 10 may include a body 12 with a surface 42 and the surface 42 may include at least one aperture 44 and or the surface may be porous and/or permeable to water. In one configuration, the mixture of PVP 14 and mitomycin 16 may be within the cavity 38 of the body 12 and the at least one aperture 44 and/or the porous/permeable surface may be permeable to water such that when the medical device 10 is inserted into tissue, the mixture of PVP 14 and mitomycin 16 may be dispersed from inside the cavity 38 to the surrounding tissue that the medical device 10 is in contact with or close to. This configuration of the medical device 10 may allow the mixture of PVP 14 and mitomycin 16 to be placed within the cavity 38 so that a medical provider does not come into contact with the mixture and then once the medical device 10 is inside the tissue, the water within the tissue can cause the mixture to disperse within the tissue.

Figure 6:
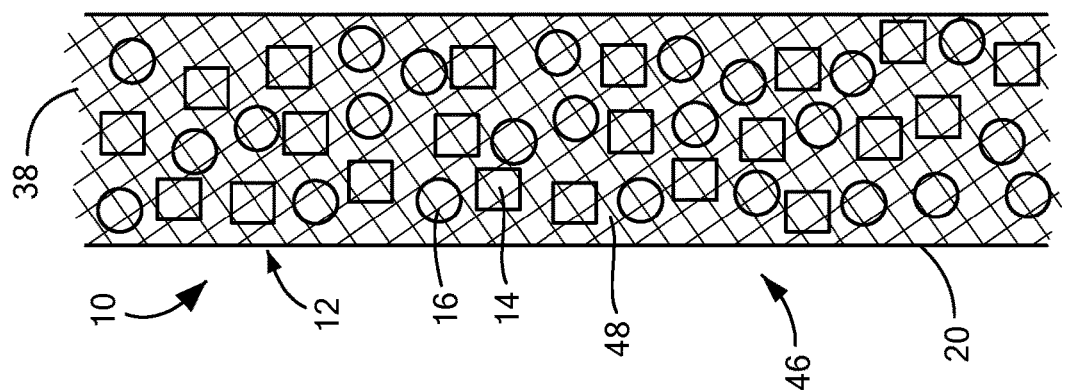
FIG. 6 illustrates another embodiment of the medical device in accordance with the present invention.

In FIG. 6, the medical device 10 may be a stent 46 which may be inserted into the lumen of an anatomic vessel or duct. The stent 46 may be a drug-eluting stent or a non-drug eluting stent and the stent 46 may be used for a variety of different medical purposes and/or procedures including cardiovascular, urological, reproductive, nephrological, neurological, ophthalmological, otolaryngologic, muscular, and for issues related to body piercings. The stent 46 may have an exterior that is mesh 48, an annular coil, a tubular shape, a ganglion-shape as well as any other shape that is appropriate for the purpose and body part that the stent 46 is going to be used within. In an exemplary embodiment, the stent 46 may be a mesh 48 stent and the mesh 48 may be coated with an exterior coating 20 which may be dissolvable once the stent 46 is inserted into tissue. The mixture of PVP 14 and mitomycin 16 may be placed in the cavity 38 within the stent 46, and once the exterior coating 20 dissolves, the mixture of PVP 14 and mitomycin 16 may be dispersed within the patient's tissue as the tissue may include water and the PVP 14 and mitomycin 16 mixture may be dissolvable in water.

In another exemplary configuration, the PVP 14 and mitomycin 16 may be coated onto the stent 46 and allowed to dry on the stent 46. Once the stent 46 is inserted into tissue, the water within the tissue may cause the coating of the PVP 14 and the mitomycin 16 to dissolve within the tissue.

Figure 7:
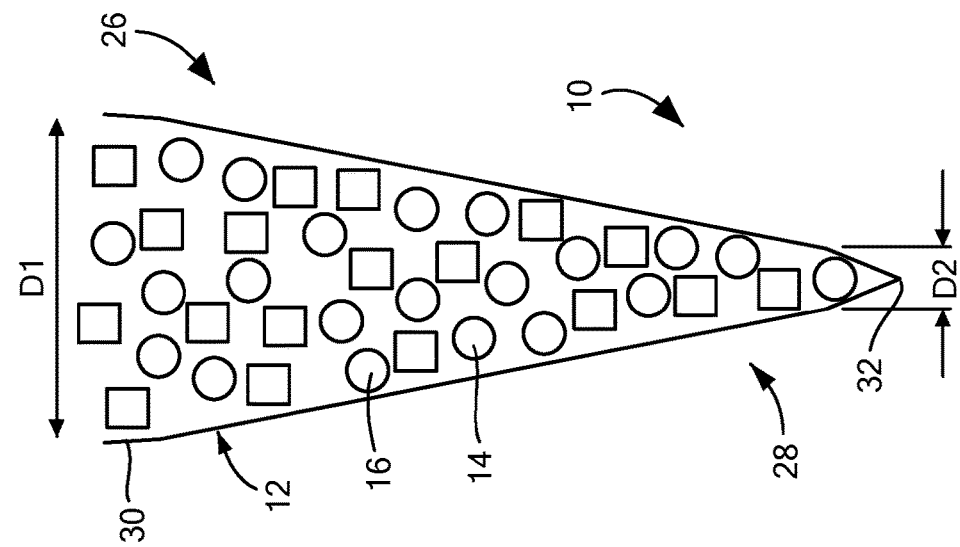
FIG. 7 illustrates another embodiment of the medical device in accordance with the present invention.

Now referring to FIG. 7, the medical device 10 may have an elongate body 12 with the first portion 26 being opposite the second portion 28. The elongate body 12 may be cylindrical and taper in diameter from the first portion 26 to the second portion 28. The first portion 26 may have a diameter D1 and the second portion 28 may have a diameter D2 that is either smaller than, equal to, or larger than the diameter D1 of the first portion 26. The first portion 26 may have a first end 30 and the first end 30 may be expandable from a first diameter to a second diameter. Alternatively, the second portion 28 may have a second end 32 and the second end 32 may be expandable from a first diameter to a second diameter as well. In alternative embodiments, the first end diameter and the second end diameter may be expandable to a variety of different diameters depending upon the tissue that the medical device 10 is being inserted into. The mixture of PVP 14 and mitomycin 16 may be coated onto at least a portion of the elongate body 12. Alternatively, the mixture of PVP 14 and mitomycin 16 may be coated on the entire elongate body 12. This coating may be covered by a bioabsorbable membrane 40 or it may simply be coated onto the elongate body 12. When the elongate body 12 is inserted into a patient's tissue, the bioabsorbable membrane 40 and the PVP and mitomycin 16 mixture may be dissolvable in the tissue.

Figure 8:
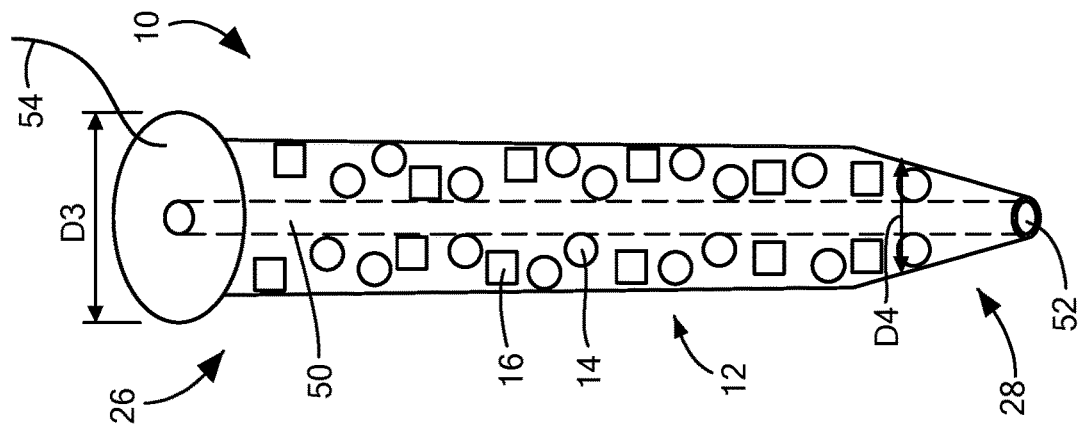
FIG. 8 illustrates another embodiment of the medical device in accordance with the present invention.

Now referring to FIG. 8 the medical device 10 may have an elongate body 12 that may be cylindrical and taper in diameter from the first portion 26 to the second portion 28. At least a portion of the first portion 26 may have a diameter D3 and at least a portion of the second portion 28 may have a diameter D4. The diameter D3 may be the widest diameter of the medical device and if the medical device 10 is inserted into a portion of the body, at least a portion of the first portion 26 may be on the exterior of the body while the second portion 28 may be in the interior of the body. The elongate body 12 may further include one or more lumens 50 thereby providing mechanical, electrical, and/or fluid communication between the first portion 26 and the second portion 28 of the medical device 10. For example, a lumen 50 may be used for the introduction and passage of a guide wire and/or a treatment or diagnostic instrument (not shown). The lumen 50 may also be used for the passage or delivery of a fluid from the first portion 26 of the medical device 10 to the second portion 28 of the medical device. The medical device 10 may further include one or more apertures 52 or openings therein, to provide for example, for the dispersion or directed ejection of fluid from the lumen 50 to the environment exterior to the lumen 50. Mitomycin 16 and PVP 14 may be coated on all or part of the medical device 10. As shown in FIG. 8, the mitomycin 16 and PVP 14 may be coated on at least a portion of the elongate body 12. The first portion may also have a removal device 54 such as a string, a suture, or a thread which can be used to remove the medical device 10 after it has been inserted into a portion of a patient's body. For example, after the medical device 10 is inserted into tissue, the removal device 54 may be pulled on to extract the medical device 10 from the patient's tissue. The medical device 10 may be made out of silicon, metal, glass, polytetrafluorethylene, polymer, plastic, and/or niobium. The medical device 10 may be used in, for example, a patient's eustachian tubes, urethra, nose, esophagus, trachea, and/or another orifice in the body.

Figure 9:
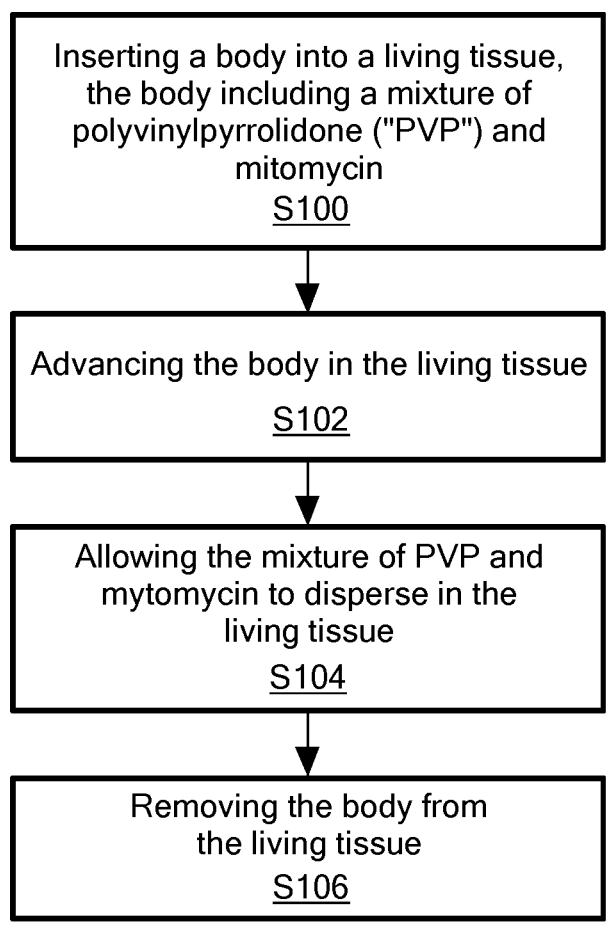
FIG. 9 is an exemplary method for inserting the medical device into living tissue.

Now referring to FIG. 9, the medical device 10 may be inserted into living tissue. The insertion of the medical device 10 into living tissue may be done with any of the embodiments discussed in FIGS. 1-8 as well as any other medical device 10 that contains a mixture of PVP 14 and mitomycin 16. As shown in S100, the body 12 may be inserted into a living tissue and the body may include a mixture of PVP 14 and mitomycin 16. This insertion may take place with a medical device 10 that has a blunted portion or a sharp portion that is configured to puncture tissue such as a pointed end. Alternatively, a needle or another device may be used to puncture the tissue and then the medical device 10 may be inserted into the tissue area that has been punctured. The body 12 may be advanced into the living tissue and this may be done quickly or slowly S102. The mixture of the PVP 14 and the mitomycin 16 will disperse into the living tissue as this mixture is water-soluble S104. The mixture of the PVP 14 and the mitomycin 16 may completely disperse into the living tissue or it may only partially disperse into the living tissue. The amount of the mixture that is dispersed may depend upon how long the medical device 10 remains within the living tissue, the material that is used with the medical device 10 and how it allows the mixture to disperse into the living tissue, as well as how much water is in the tissue. Additionally, the type of tissue that the medical device 10 is inserted into may impact how the mixture of mitomycin 16 and PVP 14 is dispersed. After the desired amount of PVP 14 and mitomycin 16 has dispersed into the tissue, the body 12 of the medical device 10 may be removed from the living tissue. S106 Alternatively, the body 12 of the medical device 10 may remain in the living tissue and/or the body 12 may dissolve in the living tissue and therefore not require the removal of the body from the living tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    a body including;
        a mixture of polyvinylpyrrolidone ("PVP") and mitomycin coated on at least a portion of the body; and
        an elongate portion having a first portion and a second portion opposite the first portion, the first portion having a rounded first end that is not coated with the mixture of PVP and mitomycin.

2. The medical device of claim 1, further comprising an exterior coating where the mixture of PVP and mitomycin is coated with the exterior coating.

3. The medical device of claim 2, wherein the exterior coating is lubricious.

4. The medical device of claim 1, wherein the second portion has a second end, the second end being expandable from a first diameter to a second diameter.

5. The medical device of claim 1, wherein the body defines a cavity, the mixture of the PVP and the mitomycin being disposed within the cavity.

6. The medical device of claim 5, further including a bioabsorbable membrane enclosing at least a portion of the cavity.

7. The medical device of claim 6, wherein the body has a surface, the surface including at least one aperture.

8. The medical device of claim 1, wherein the body is a stent.

9. The medical device of claim 1, wherein the mixture of PVP and mitomycin further includes at least one selected from the group consisting of alginate, karaya gum, cellulose ether, gelatin, and polyvinyl alcohol.

10. A medical device, comprising:
    a body including:
        an elongate portion having:
            a first portion having a rounded first end;
            a second portion opposite the first portion; and
            a longitudinal axis defined therebetween, the second portion being transitionable between a first retracted configuration and a second extended configuration along the longitudinal axis, the second portion extending farther away from the first portion when in the second extended configuration than when in the first retracted configuration; and
        a mixture of polyvinylpyrrolidone (PVP) and mitomycin.

11. A medical device, comprising:
    a body including a mixture of polyvinylpyrrolidone ("PVP") and mitomycin, the mixture including:
        approximately 1.0 mg/g of a mitomycin solution having:
            approximately 30.0 mg of mitomycin; and
            approximately 29.970 mg of absolute ethanol;
        approximately 1.360 g of PVP; and
        approximately 0.090 g of a PVP copolymer.

12. The medical device of claim 11, wherein the mixture of PVP and mitomycin further includes at least one selected from the group consisting of alginate, karaya gum, cellulose ether, gelatin, and polyvinyl alcohol.

13. The medical device of claim 9, wherein the cellulose ether is one selected from hydroxyethyl cellulose and hydroxypropyl cellulose.

14. The medical device of claim 12, wherein the cellulose ether is one selected from hydroxyethyl cellulose and hydroxypropyl cellulose.

* * * * *

UNITED STATES PATENT AND TRADEMARK OFFICE
CERTIFICATE OF CORRECTION

| | | |
|---|---|---|
| PATENT NO. | : 11,207,267 B2 | Page 1 of 1 |
| APPLICATION NO. | : 16/591005 | |
| DATED | : December 28, 2021 | |
| INVENTOR(S) | : Bruce Segal and Nelson Landrau | |

It is certified that error appears in the above-identified patent and that said Letters Patent is hereby corrected as shown below:

On the Title Page

On page 2, Column 2, item (56) OTHER PUBLICATIONS Line 19, replace "Mi et al." with -- Ali et al. --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*